US00PP21891P2

(12) United States Plant Patent

Herring et al.

(10) Patent No.: US PP21,891 P2

(45) Date of Patent: May 3, 2011

(54) *NANDINA DOMESTICA* PLANT NAMED 'SEIKA'

(50) Latin Name: *Nandina domestica*
Varietal Denomination: Seika

(75) Inventors: April Herring, The Woodlands, TX (US); Adriana Garza, Magnolia, TX (US)

(73) Assignee: TNM Corporation, Waller, TX (US)

( * ) Notice: Subject to any disclaimer, the term of this patent is extended or adjusted under 35 U.S.C. 154(b) by 0 days.

(21) Appl. No.: 12/661,085

(22) Filed: Mar. 9, 2010

(51) Int. Cl.
*A01H 5/00* (2006.01)

(52) U.S. Cl. ..... Plt./235

(58) Field of Classification Search ..... Plt./235
See application file for complete search history.

(56) References Cited

U.S. PATENT DOCUMENTS

PP5,656 P 2/1986 Barr
PP5,659 P 2/1986 Barr

*Primary Examiner* — Annette H Para

(74) *Attorney, Agent, or Firm* — Christie, Parker & Hale, LLP

(57) ABSTRACT

'SEIKA', a new and distinct variety of *Nandina domestica*, characterized by its tight, dense upright plant habit; slow growth rate; and unique deep red-colored young foliage and deep green-colored mature foliage. Deep red color of young foliage is retained while the plant is actively growing.

10 Drawing Sheets

Classification: The present invention relates to a new *Nandina domestica* plant.

Variety denomination: The new plant has the varietal denomination 'SEIKA'.

BACKGROUND OF THE INVENTION

The present Invention relates to a new and distinct cultivar of *Nandina* plant, botanically known as *Nandina domestica*, a member of the Berberidaceae family, commonly known as Heavenly Bamboo.

This new 'SEIKA' variety resulted from a naturally occurring, whole plant mutation discovered in a cultivated planting of the *Nandina domestica* variety 'Gulf Stream' (U.S. Plant Pat. No. 5,656). 'SEIKA' appeared different from 'Gulf Stream' plants growing in 72 cell tray in a greenhouse in Magnolia, Tex. and was initially discovered around July 2005 by the inventors.

The selection of this plant was based on its unique and long-lasting deep red-colored young foliage in contrast to the typical bronze-green-colored young foliage of the cultivar *Nandina domestica* 'Gulf Stream' (U.S. Plant Pat. No. 5,656).

The new variety was first reproduced by asexual propagation (micropropagation) at Magnolia Gardens Nursery, Magnolia, Tex. It has since been reproduced numerous times at Magnolia Gardens Nursery, Magnolia, Tex. by asexual propagation (micropropagation). Using this method of asexual propagation it takes 2-3 weeks to initiate root development. Each of the progeny exhibit identical characteristics to the original mutant plant, showing that the unique features of this new *Nandina* are stable and reproduced true to type in successive generations.

SUMMARY OF THE INVENTION

Plants of the new *Nandina* have not been observed under all possible environmental conditions. The phenotype may vary somewhat with variations in environment such as temperature, day length, light intensity, nutrition and water status without, however, any variance in genotype. The following observations and descriptions are of 2.5-year-old plants grown in a landscape in Magnolia, Tex.

The following traits have been repeatedly observed and are determined to be the unique characteristics of 'SEIKA'. These characteristics in combination distinguish 'SEIKA' as a new and distinct cultivar:

1. Dense, compact and upright plant habit.
2. Slow growth rate.
3. Unique deep red-colored young foliage and deep green-colored mature foliage. Deep red color of young foliage is retained while the plants are actively growing.

The 'SEIKA' cultivar has been observed and extensively tested in different growing situations for four years. Its recognizable characteristics, which distinguish it from other known *Nandina* cultivars are:

1. Compact, dense form, with a mature height of 24-30".
2. Slow growth rate.
3. Has proven adaptable to harsh environmental conditions.
4. Flowers have been observed but no fruit has been observed to date.
5. Exhibits unique leaf coloration. New growth is deep red. Mature winter foliage is bronze red.
6. Is sun and shade tolerant maintaining its proportions equally well in both conditions.

COMPARISON WITH PARENT

The parent cultivar to the new *Nandina* is the cultivar 'Gulf Stream' (disclosed in U.S. Plant Pat. No. 5,656). Plants of the new *Nandina* may be distinguished from the cultivar 'Gulf Stream' by the following characteristic as seen in side-by-side comparisons conducted in Magnolia Tex. Plants of the new *Nandina* differed from plants of the cultivar 'Gulf Stream' primarily in developing foliage coloration as plants of the new *Nandina* produced deep red-colored leaves, Greyed-Purple Group 183A whereas plants of the cultivar 'Gulf Stream' produced bronze-green-colored leaves, Yellow-Green Group 153B.

COMPARISON WITH THE CLOSEST COMMERCIALLY AVAILABLE CULTIVAR

The closest commercially available cultivar to the new *Nandina* is the cultivar 'Moon Bay' (disclosed in U.S. Plant Pat. No. 5,659. Plants of the new N*andina* differed from plants of the cultivar 'Moon Bay' primarily in developing foliage coloration as plants of the new *Nandina* produced deep red-colored leaves. Greyed-Purple Group 183A whereas plants of the cultivar 'Moon Bay' produced lime green-colored leaves, Yellow-Green Group 145A. It has also been observed that plants of the new *Nandina* are larger as a mature plant at 24-30" tall and 20-24" wide, whereas plants of the cultivar 'Moon Bay' are smaller as a mature plant at 20" tall and 15" wide on average.

BRIEF DESCRIPTION OF ILLUSTRATIONS

FIG. 1-A is a color photograph of the original plant 'SEIKA' growing in a 72 cell tray with the 'Gulf Stream' (U.S. Plant Pat. No. 5,656) crop it was found with at 8 weeks of age.

FIG. 1-B represents the same plant as FIG. 1-A, but 4 months later in a 1 gallon container.

FIG. 2-A is a side-by-side comparison of the new variety, shown on the right, with a 'Gulf Stream' (U.S. Plant Pat. No. 5,656) shown on the left to illustrate the difference in color of the new growth. Both plants are liners in a 72 cell tray.

FIG. 2-B is a side-by-side comparison of the new variety, shown on the left, with a 'Gulf Stream' (U.S. Plant Pat. No. 5,656) shown on the right to illustrate the difference in color of the new growth. Both plants are in a 3-gallon container.

FIG. 2-C is a side-by-side comparison of the new variety, shown on the bottom of the frame, with a 'Gulf Stream' (U.S. Plant Pat. No. 5,656) shown on bottom half of the frame. Both plants are in a landscape setting at approximately 18 months of age.

FIG. 2-D is a side-by-side comparison of the new foliage of the new variety, shown on the left, with the new foliage of 'Gulf Stream' (U.S. Plant Pat. No. 5,656) shown on the right.

FIG. 3-A is a side-by-side comparison of the new variety, shown on the left, with a 'Moon Bay' (U.S. Plant Pat. No. 5,659) shown on the right to illustrate the difference in color of the new growth. Both plants are in a 3 gallon container.

FIG. 3-B is a side-by-side comparison of the new foliage of the new variety, shown on the left, with the new foliage of 'Moon Bay' (U.S. Plant Pat. No. 5,659) shown on the right.

FIG. 4-A is a photograph of the new variety at 18 months old growing in a landscape setting in Magnolia, Tex. This photo shows the unique leaf coloration in the spring.

FIG. 5-A is a photograph of the first crops of the new variety in a 72 cell tray propagated by tissue culture showing the uniformity. It also shows the unique color of the new growth. Picture taken in the summer

DETAILED BOTANICAL DESCRIPTION

In the following description, color references are made to The Royal Horticultural Society Colour Chart except where general terms of ordinary dictionary significance is used. The following observations and measurements describe plants grown in a landscape setting in Magnolia, Tex.

Botanical classification: *Nandina domestica* cultivar 'SEIKA'.

Parentage: A naturally occurring, whole plant mutation originating in an asexually produced (micropropagated) population of *Nandina domestica* 'Gulf Stream' (U.S. Plant Pat. No. 5,656).

Propagation: Type.—By tissue culture or micropropagation. Rooting habit.—Numerous, fibrous, root initiation seen in 2-3 weeks.

Plant description: Appearance: Dwarf, symmetrical, densely compact, solitary form. Slow in growth with an upright habit and unique foliage coloration.

Mature plant height: 24-30 inches.

Mature plant width: 20-24 inches.

Stems:

- *Stem Diameter.*—8-10 mm.
- *Internode length.*—10-12 mm.
- *Stem color.*—Young Stems: Closest to Green Group 137B. Mature Stems: Closest to Brown Group 200C.
- *Stem length.*—14-16 cm.
- *Stem form.*—Upright.
- *Stem texture.*—Smooth, longitudinally ridged.
- *Branching habit.*—Branches freely from the basal buds.

Foliage description: Evergreen.

- *Arrangement.*—Alternate, Odd tripinnately Compound.
- *Leaf length.*—30-36 cm.
- *Leaf width.*—56-60 cm.
- *Petiole diameter.*—2-3 mm.
- *Petiole length.*—4-5 cm.
- *Petiole color.*—Petioles on Young Foliage: Closest to Greyed-Red Group 178A. Petioles on Intermediate Foliage: Closest to Green Group 137B. Petioles on Mature Foliage: Closest to Green Group 137A.
- *Petiolule diameter.*—1 mm on average.
- *Petiolule length.*—1 mm on average.
- *Petiolule color.*—Petiolules on Young Foliage: Closest to Greyed-Red Group 178A. Petiolules on Intermediate Foliage: Closest to Green Group 137B. Petiolules on Mature Foliage: Closest to Green Group 137A.

Leaflets:

- *Leaflet base.*—Cuneate. Leaflet tips — Acute.
- *Leaflet shape.*—Lanceolate.
- *Leaflet margin.*—Entire.
- *Leaflet venation pattern.*—pinnate.
- *Leaflet length.*—2-6 cm.
- *Leaflet width.*—1-2.5 cm.
- *Leaflet texture.*—Upper surface: Glaborous. Lower surface: Glaucous.
- *Leaflet aspect.*—Cupped or reflexed.

Color:

- *Young leaflets.*—Upper Side: Closest to Greyed Purple Group 183A. Lower Side: Closest to Greyed Orange Group 176B.
- *Intermediate leaflets.*—Upper Side: Closest to Greyed Orange Group 177A. Lower Side: Closest to Greyed-Green Group 176B.
- *Mature leaflets.*—Upper Side: Closest to Greyed-Green Group N189A. Lower Side: Closest to Green Group 137B.
- *Winter color.*—Closest to Greyed-Purple Group 187A.
- *Vein color.*—Veins on Young Leaflets: Closest to Greyed-Orange Group 166A. Veins on Intermediate Leaflets: Closest to Green Group 137B. Veins on Mature Leaflets: Closed to Green Group 137B.

Inflorescence: Inflorescence is typical of the variety *Nandina domestica* 'Gulf Stream' (U.S. Plant Pat. No. 5,656).

*Description.*—Inflorescence borne on terminal erect stalked panicles, consisting of 150 to 220 individual perfect flowers. Inflorescence conical in shape. Individual flowers, actinomorphic with 6 white petals. Closest to White Group 155B. Petals are elliptic with an entire margin.

*Inflorescence bud.*—Length: 4-5 mm. Diameter: 2-3 mm. Closest to White Group 155A.

*Inflorescence size.*—Panicle. — Height: about 14-16 cm. Width: about 8-9 cm.

*Individual flower.*—Diameter about 10 mm. Petals. — Length: 4 mm. Width: 3 mm.

*Reproductive organs.*—Androecium. — 6 stamens. Length about 3 mm. Closest to Yellow Group 15A. The filament is insignificant as to be not visible. Gynoecium.—Pistil superior. Length about 3 mm. Width about 1-2 mm.

*Ovary.*—Color Closest to Orange-White Group 159C.

*Style.*—Color Closest to Orange-White Group 159D.

*Stigma.*—Closest to Orange Group 29A.

*Blooming duration.*—5 to 7 days.

*Bloom lastingness.*—1 to 2 days. Fragrance: None.

Seed production: To date, production of berries or seeds has not been observed.

Disease resistance: Resistance to diseases common to plants of *Nandina* has not been observed.

Pest resistance: Resistance to pests common to plants of *Nandina* has not been observed.

We claim:

1. A new and distinct cultivar of *Nandina domestica* plant named 'SEIKA', as illustrated and described.

* * * * *

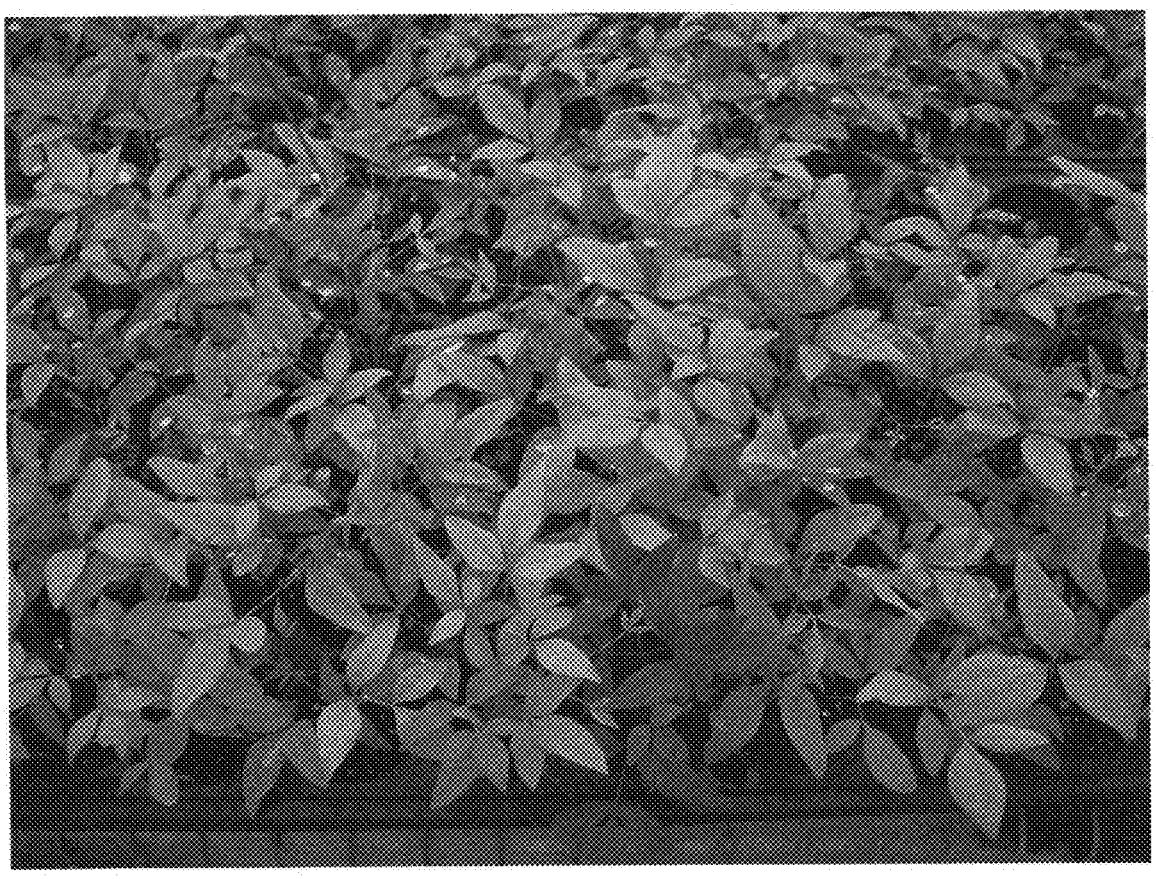
FIG. 1-A

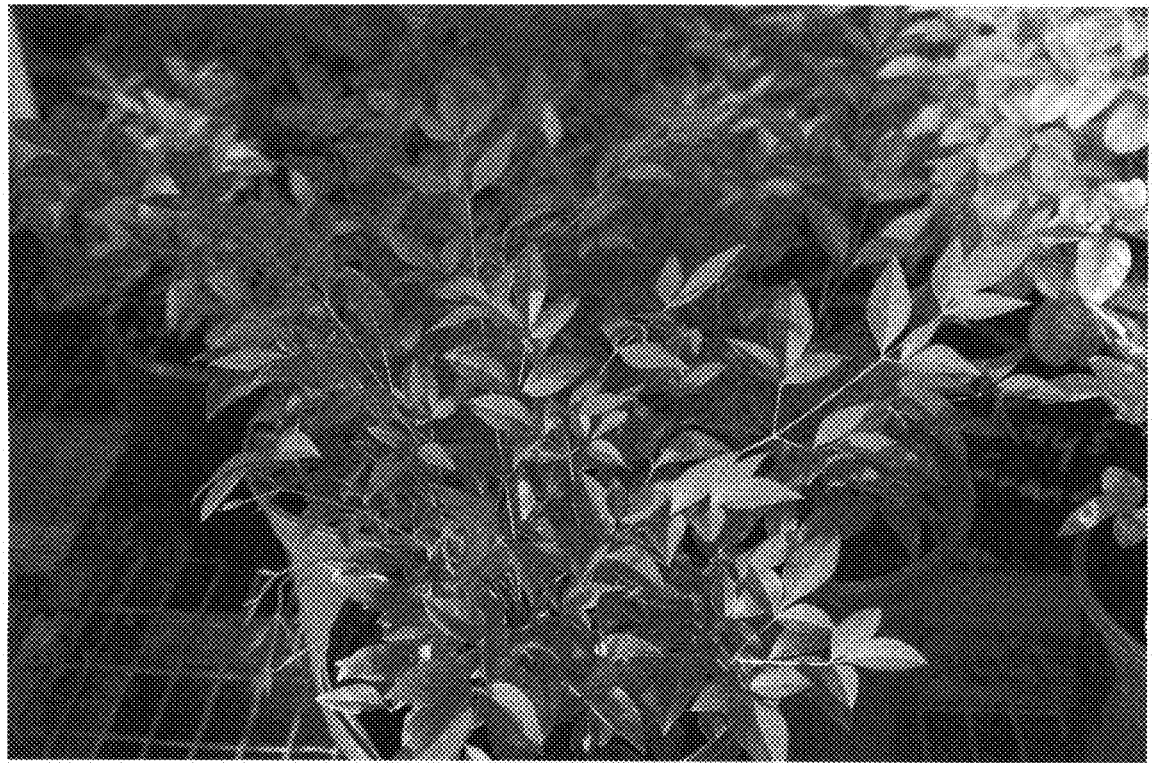
FIG. 1-B

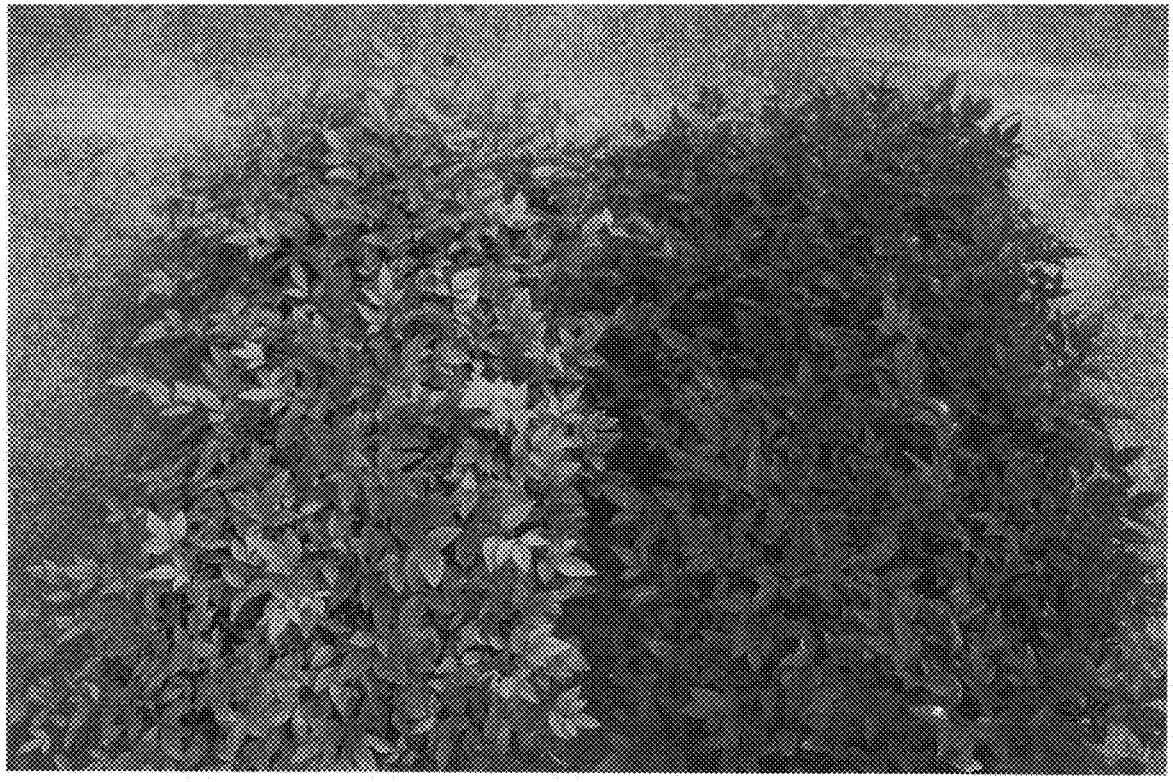
FIG. 2-A

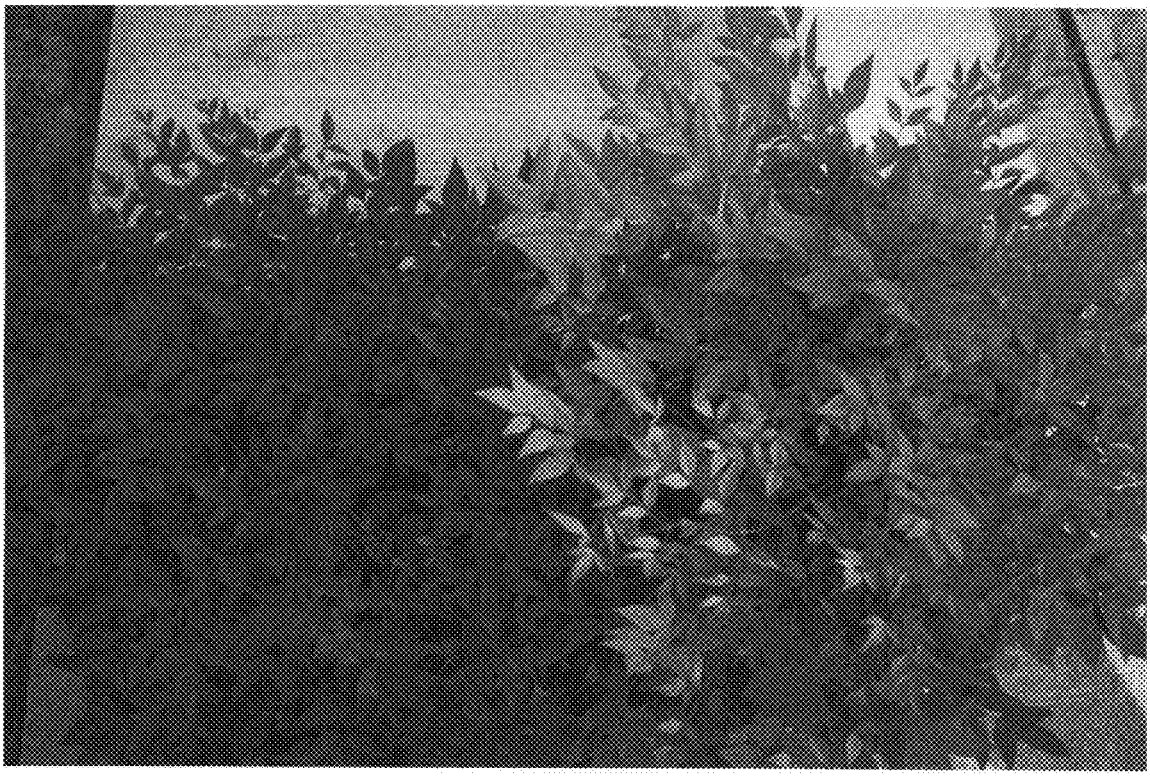
FIG. 2-B

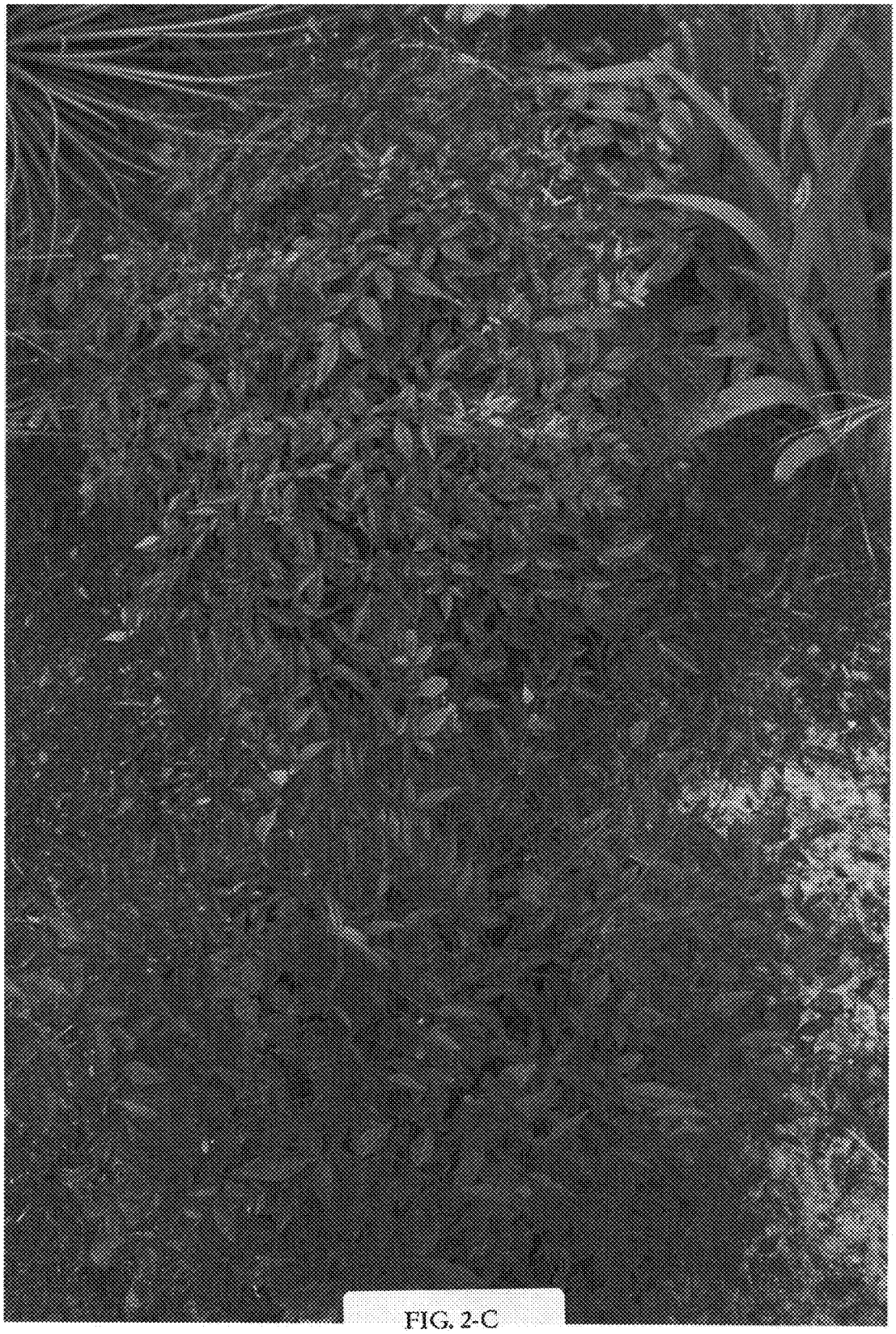
FIG. 2-C

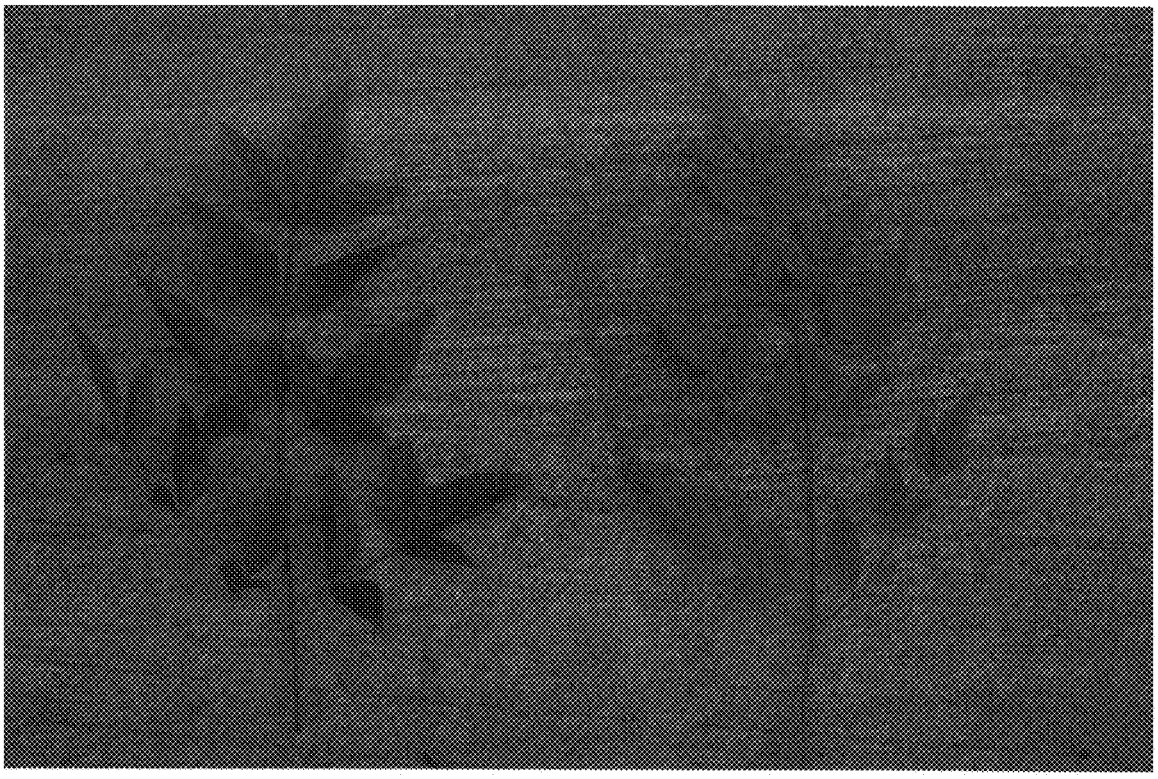
FIG. 2-D

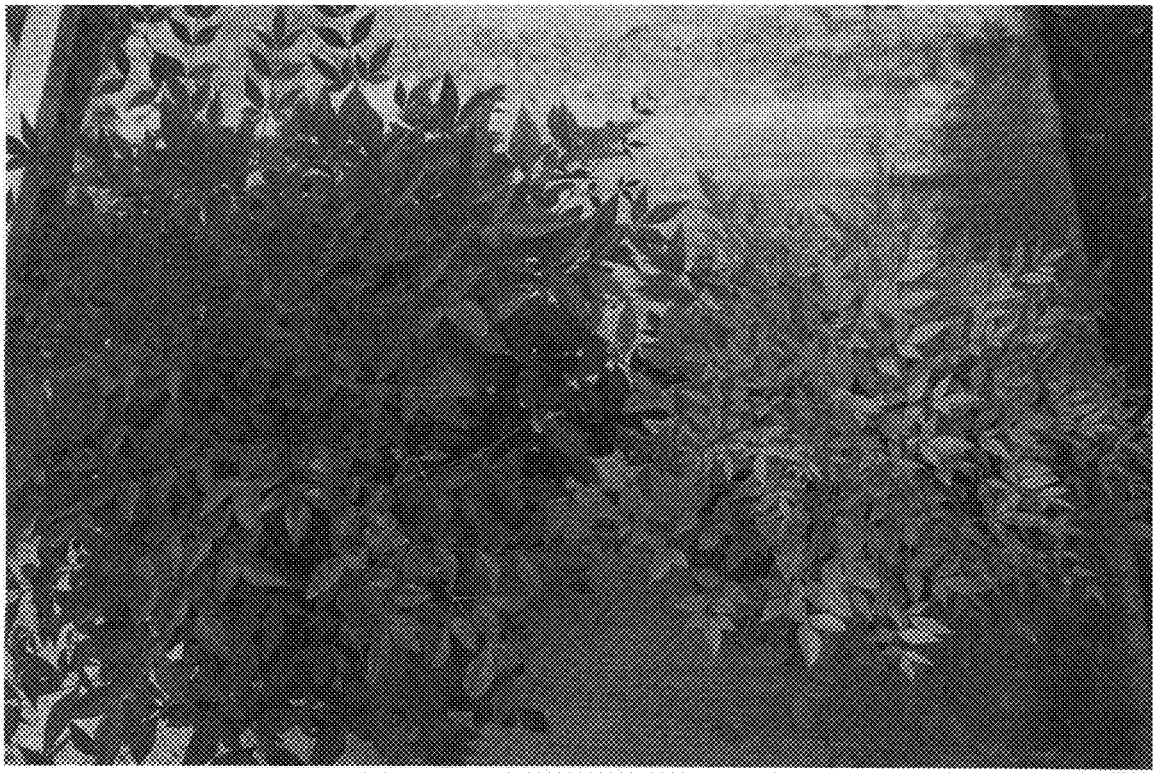
FIG. 3-A

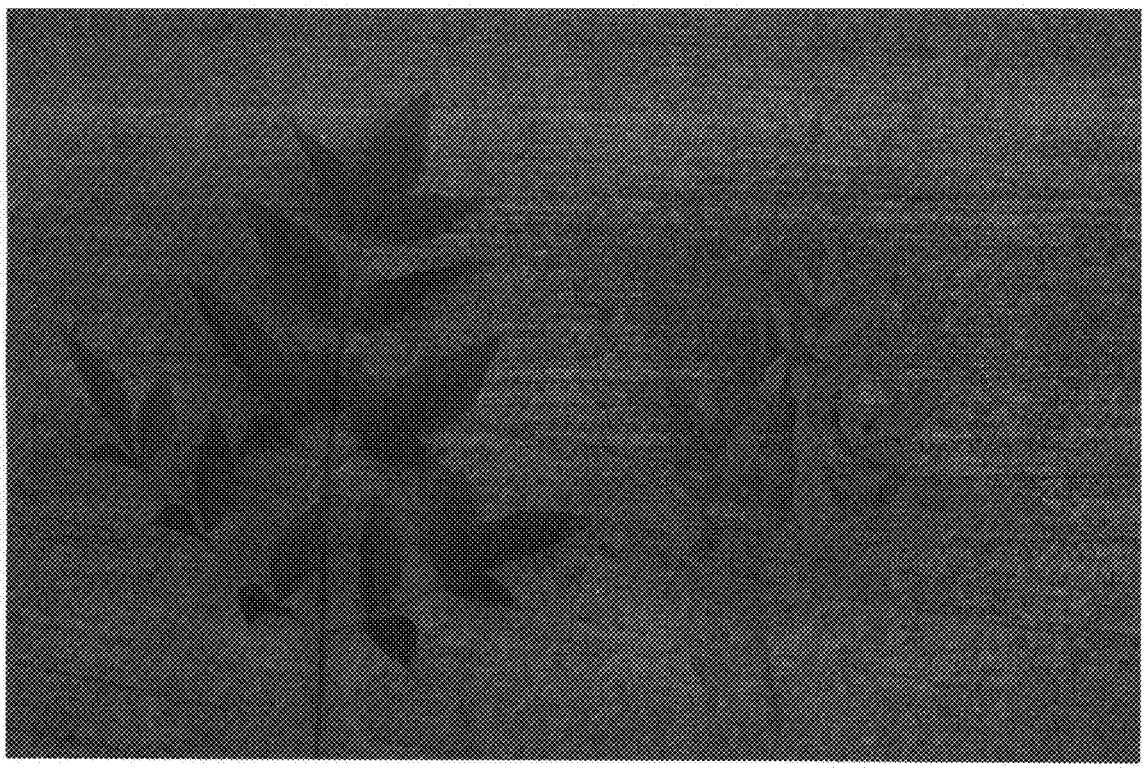
FIG. 3-B

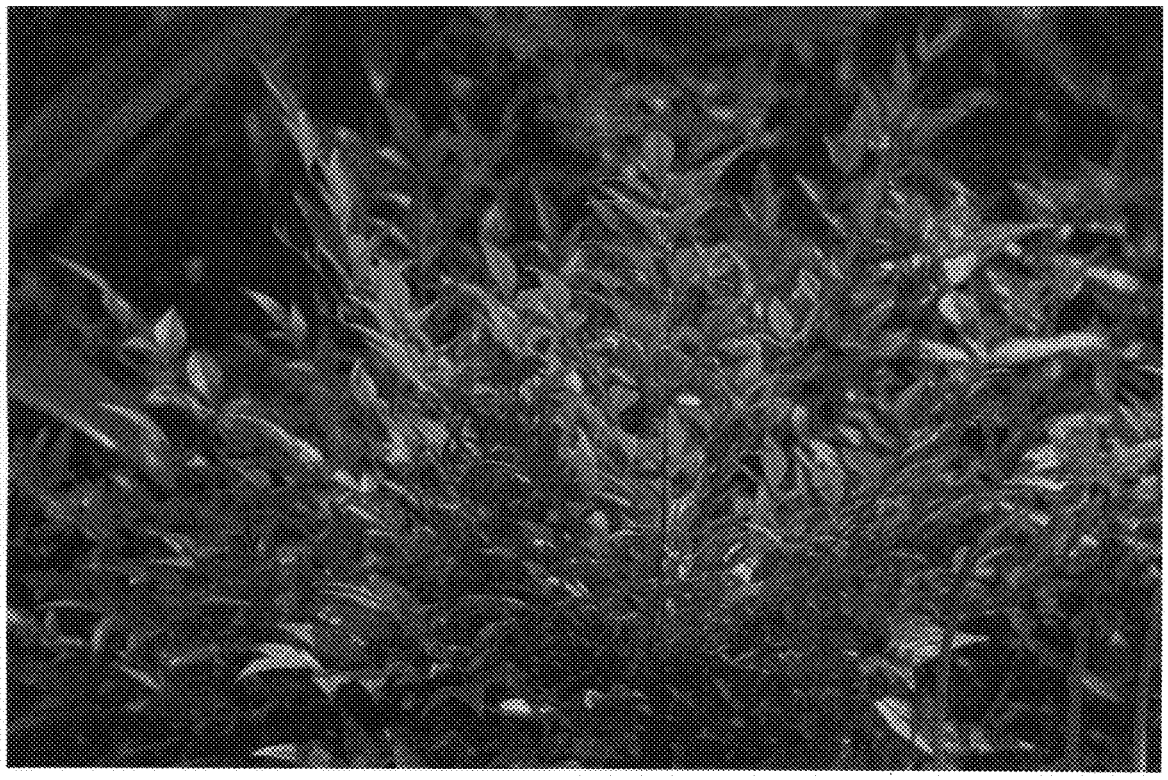
FIG. 4-A

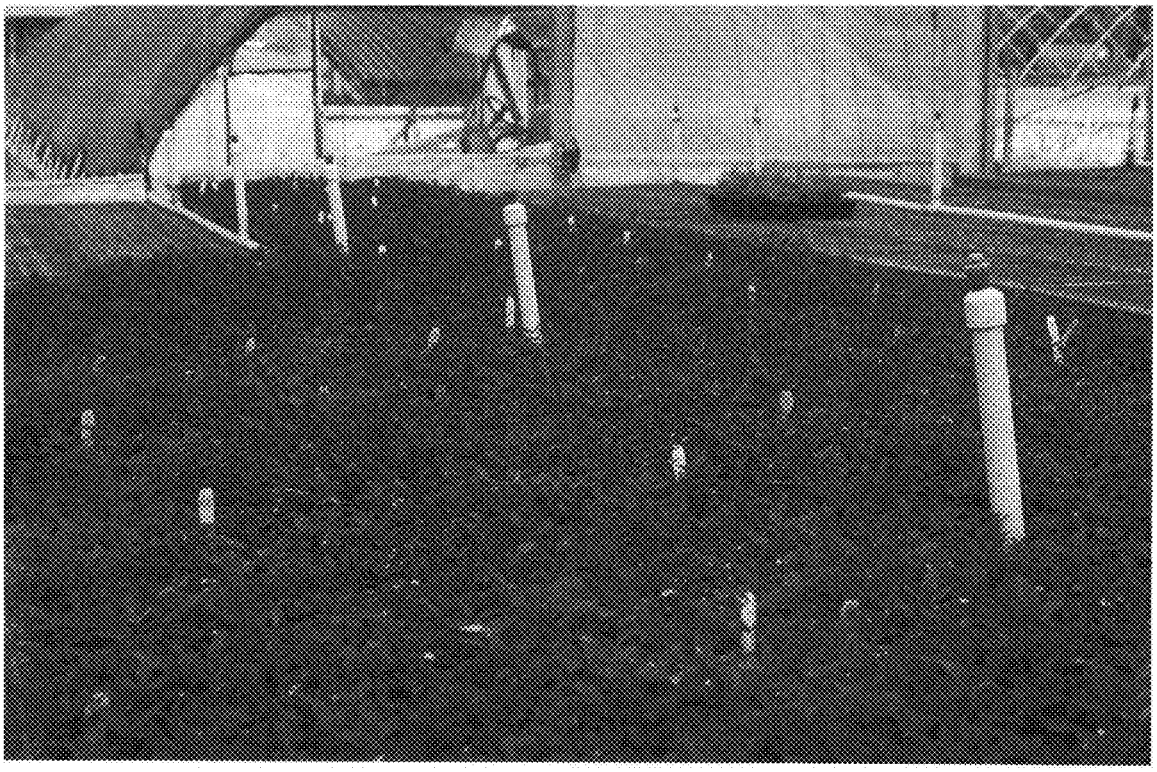
FIG. 5-A